(12) United States Patent
He et al.

(10) Patent No.: US 10,985,321 B2
(45) Date of Patent: Apr. 20, 2021

(54) SEMICONDUCTING CO-POLYMERS OF METHYLENEDIHYDROPYRAZINES WITH FUSED THIOPHENES

(71) Applicant: CORNING INCORPORATED, Corning, NY (US)

(72) Inventors: Mingqian He, Horseheads, NY (US); James Robert Matthews, Painted Post, NY (US); Weijun Niu, Painted Post, NY (US); Adama Tandia, Nelson, PA (US); Arthur Lawrence Wallace, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 16/555,548

(22) Filed: Aug. 29, 2019

(65) Prior Publication Data
US 2020/0075865 A1    Mar. 5, 2020

Related U.S. Application Data

(60) Provisional application No. 62/724,214, filed on Aug. 29, 2018.

(51) Int. Cl.
| | |
|---|---|
| *H01L 51/05* | (2006.01) |
| *H01L 51/42* | (2006.01) |
| *C07D 495/22* | (2006.01) |
| *C08L 65/00* | (2006.01) |
| *C09D 165/00* | (2006.01) |
| *H01L 51/00* | (2006.01) |
| *C08G 61/12* | (2006.01) |

(52) U.S. Cl.
CPC ........ *H01L 51/0036* (2013.01); *C08G 61/126* (2013.01); *H01L 51/0043* (2013.01); *C08G 2261/124* (2013.01); *C08G 2261/1412* (2013.01); *C08G 2261/1424* (2013.01); *C08G 2261/22* (2013.01); *C08G 2261/334* (2013.01); *C08G 2261/414* (2013.01); *C08G 2261/51* (2013.01); *C08G 2261/91* (2013.01); *C08G 2261/92* (2013.01); *C08G 2261/94* (2013.01); *C08G 2261/95* (2013.01); *H01L 51/0545* (2013.01); *H01L 51/0558* (2013.01)

(58) Field of Classification Search
CPC ............. H01L 51/0036; H01L 51/0043; H01L 51/0545; H01L 51/0558; H01L 51/4206; H01L 51/00; C08G 61/126; C08G 2261/124; C08G 2261/1412; C08G 2261/1424; C08G 2261/22; C08G 2261/334; C08G 2261/414; C08G 2261/51; C08G 2261/91; C08G 2261/92; C08G 2261/94; C08G 2261/95; C08G 2261/3323; C08G 2261/364; C08L 65/00; C09D 165/00; C07D 495/22; Y02E 10/549

See application file for complete search history.

(56) References Cited

U.S. PATENT DOCUMENTS

| | | | |
|---|---|---|---|
| 7,838,623 | B2 | 11/2010 | He |
| 8,278,346 | B2 | 10/2012 | He et al. |
| 2009/0218564 | A1 | 9/2009 | Park et al. |
| 2013/0085256 | A1 | 4/2013 | He et al. |
| 2013/0109821 | A1 | 5/2013 | He et al. |
| 2015/0065722 | A1 | 3/2015 | He et al. |

FOREIGN PATENT DOCUMENTS

| | | |
|---|---|---|
| WO | 2006031893 A2 | 3/2006 |
| WO | 2008106019 A2 | 9/2008 |
| WO | 2009123695 A1 | 10/2009 |

OTHER PUBLICATIONS

Allard et al; "Organic Semiconductors for Solution-Processable Field-Effect Transistors (OFETs)" ; Angew. Chem. Int. Ed. 2008, 47, 4070-1098.
Ando et al; "Diastereoselective Synthesis of Diketopiperazine Bis-a,—Epoxides" ; J. Org. Chem. 2011, 76, pp. 1155-1158.
Bronstein et al; "Thieno[3,2-b]Thiophene-Diketopyrrolopyrrole-Containing Polymers for High-Performance Organic Field-Effect Transistors and Orgainc Photovoltaic Devices" ; J. Am. Chem. Soc.; 2011, 133 pp. 3272-3275.
Fong et al; "Tetrathienoacene Copolymers as High Mobility, Soluble Orgainc Semiconductors" ; J. Am. Chem. Soc. 2008, 130, pp. 13202-13203.
Fu et al; "Enhancing Field-Effect Mobility of Conjugated Polymers Through Rational Design of Branched Side Chains" ; Adv. Funct. Mater. 2014, 24, pp. 3734-3744.
Guo et al; "Current Status and Opportunities of Organic Thin-Film Transistor Technologies" ; IEEE Transactions on Electron Devices, vol. 64, No. 5, May 2017; pp. 1906-1921.
He et al; "Alkylsubstituted Thienothiophene Semiconducting Materials:; Structure-Property Relationships" ; J. Am. Chem. Soc. 2009, 131, 11930-11938.
Holliday et al; "Advances in Charge Carrier Mobilites of Semiconducting Polymers Used in Organic Transistors" ; Chem. Mater. 2014, 26, pp. 647-663.
International Search Report and Written Opinion of the International Searching Authority; PCT/US2019/047453; dated Oct. 21, 2019; 12 Pages; European Patent Office.

(Continued)

*Primary Examiner* — John M Mauro

(57) ABSTRACT

Compositions are included comprising heterocyclic organic compounds based on fused thiophene compounds, polymers based on fused thiophene compounds, and methods for making the monomers and polymer along with uses in thin film-based and other devices.

23 Claims, 1 Drawing Sheet

(56) References Cited

OTHER PUBLICATIONS

Kang et al; "Record High Hole Mobility in Polymer Semiconductor via Side-Chain Engineering" ; J. Am. Chem. Soc., 2013; 135; pp. 14896-14899.

Kanimozhi et al; "Diketopyrrolophrrole-Diketopyrrolopyrrole-Based Conjugated Copolymer for High-Mobility Organic Field-Effect Transistors" ; J. Am. Chem. Soc.; 2012, 134, pp. 16532-16535.

Katz; "Recent Advances in Semiconductor Performance and Printing Processes for Organic Transistor-Based Electronics" ; Chem. Mater. 2004, 16, pp. 4748-4756.

Lei et al; "Influence of Alkyl Chain Branching Positions on the Hole Mobilities of Polymer Thin-Film Transistors" ; Adv. Mater. 2012, 64, pp. 6457-6461.

Li et al; "A High Mobility P-Type DPP-Thieno[3,2-b]Thiophene Copolymer for Organic Thin-Film Transistors" ; Adv. Mater. 2010, 22, pp. 4862-4866.

Liu et al; "para-Azaquinodimethane: A Compact Quinodimethan Variant as an Ambient Stable Building Block for High-Performance Low Band Gap Polymers" ; J. Am. Chem. Soc. 2017, 139, 8355-8363.

Liu et al; "Para-Azaquinodimethane: A Compact Quinodimethan Variant as an Ambient Stable Building Block for High-Performance Low Band Gap Polymers" ; J. Am. Chem. Soc. 2017, 139, 8355-8363—Supporting Information.

Liu et al; "Unraveling the Main Chain and Side Chain Effects on Thin Film Morphology and Charge Transport in Quinoidal Conjugated Polymers" ; Adv. Funct. Mater. 2018, 28, 2 Pages.

Matthews et al; "Scalable Synthesis of Fused Thiophene-Diketopyrrolopyrrole Semiconducting Polymers Processed From Nonchlorinated Solvents Into High Performance Thin Film Transistors" ; Chem. Mater. 2013, 25, pp. 782-789.

Meager et al; "Photocurrent Enhancement From Diketopyrrolopyrrole Polymer Solar Cells Through Alkyl-Chain Branching Point Manipulation" ; J. Am. Chem. Soc. 2013; 135; pp. 11537-11540.

Sirringhaus et al; "Two-Dimensional Charge Transport in Self-Organized, High-Mobility Conjugated Polymers" ; Nature, vol. 401, 1999; pp. 685-688.

Street; "Unraveling Charge Transport in Conjugated Polymers" ; Science; vol. 341; 2013; pp. 1072-1073.

Sun et al; "Record High Electron Mobility of 6.3 cm2V-1S-1 Achieved for Polymer Semiconductors Using a New Building Block" ; Adv. Mater. 2014, 26, pp. 2636-2642.

Tsao et al; "Ultrahigh Mobility in Polymer Field-Effect Transistors by Design" ; J. Am. Chem. Soc. 2011, 133; pp. 2605-2612.

Tseng et al; "High-Mobility Field-Effect Transistors Fabricated With Macroscopic Aligned Semiconducting Polymers" ; Adv. Mater. 2014, 26, pp. 2993-2998.

Unver et al; "Synthesis of New Donor-Acceptor Polymers Containing Thiadiazoloquinoxaline and Pyrazinoquinoxaline Moieties: Low-Band Gap, High Optical Contrast, and Almost Black Colored Materials" ; Tetrahedron Letters; 52 (2011) pp. 2725-2729.

Yun et al; "Conformation-Insensitive Ambipolar Charge Transport in a Diketopyrrolopyrrole-Based Co-Polymer Containing Acetylene Linkages" ; Chem. Mater. 2014; 26; pp. 3928-3937.

Ando et al; "Supporting Information for Diastereoselective Synthesis of Diketopiperazine Bis-a, —Epoxides" ; 2011; 70 Pages; URL:https://pubs.acs.org/doi/suppl/10.1021.

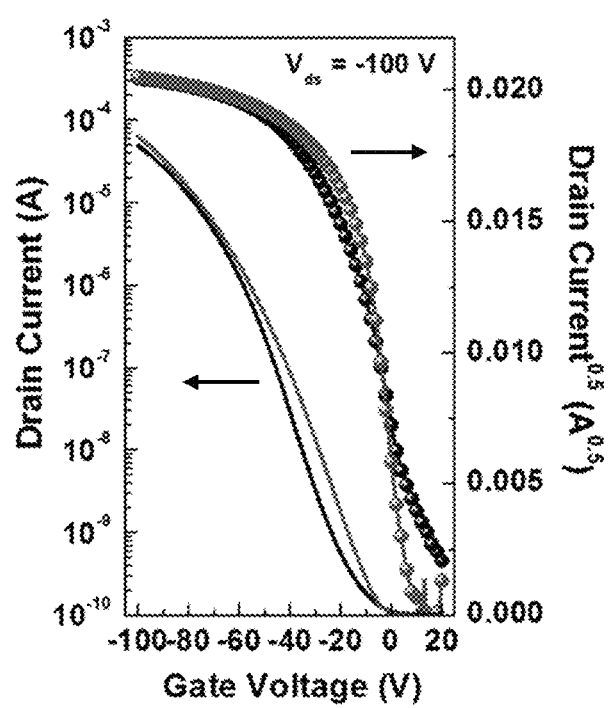

SEMICONDUCTING CO-POLYMERS OF METHYLENEDIHYDROPYRAZINES WITH FUSED THIOPHENES

CROSS REFERENCE TO RELATED APPLICATIONS

This application claims the benefit of priority under 35 U.S.C. § 119 of U.S. Provisional Application Ser. No. 62/724,214, filed on Aug. 29, 2018, the content of which is relied upon and incorporated herein by reference in its entirety.

BACKGROUND

1. Field

The disclosure relates to fused thiophene-based semiconducting polymers employing high efficiency dialkoxydimethylenedihydropyrazine (AMDHP) group electron acceptor.

2. Technical Background

Highly-conjugated organic materials are currently the focus of great research activity due to their interesting electronic and optoelectronic properties and potential cost savings over their inorganic counterparts (e.g., silicon). For example, organic semiconductors may be used as functional materials in printed electronics, organic transistors (thin film, field effect, etc.), organic light-emitting diodes (OLEDs), organic integrated circuits, and organic solar cells. Potential applications include, for example, smart cards, security tags, low cost sensors, and the switching elements in the backplane of flat panel displays.

Performances of devices comprising organic semiconductor materials may be evaluated by charge carrier mobility, current on/off ratio, threshold voltage, and magnitude of the on/off current. Currently available materials often suffer from low solubility, marginal processing ability and oxidative instability, which may lead to low performance electrical metrics.

This disclosure presents improved fused thiophene-based semiconducting polymers and methods of fabrication thereof for organic semiconductor (OSC) layers of organic thin-film transistors (OTFTs).

SUMMARY

In some embodiments, a composition comprises a dialkoxydimethylenedihydropyrazine (AMDHP) fused-thiophene (FT) organic semiconductor polymer having a repeat unit of Formula 2 or Formula 3, or a salt, isomer, or analog thereof:

Formula 2

Formula 3 wherein m is an integer greater than or equal to zero; wherein n is an integer greater than or equal to one; X and Y are, independently, a covalent bond or aryl; A and B are, independently, a nitrogen group or a C—H group; $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted; $R_3$ and $R_4$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted; and p and q are, independently, integers greater than or equal to zero.

In one aspect, which is combinable with any of the other aspects or embodiments, A and B are nitrogen.

In one aspect, which is combinable with any of the other aspects or embodiments, at least one of $R_1$ and $R_2$ comprises a substituted or unsubstituted alkyl.

In one aspect, which is combinable with any of the other aspects or embodiments, at least one of $R_1$ and $R_2$ comprises an unsubstituted alkyl.

In one aspect, which is combinable with any of the other aspects or embodiments, at least one of $R_3$ and $R_4$ comprises a substituted or unsubstituted alkyl.

In one aspect, which is combinable with any of the other aspects or embodiments, at least one of $R_3$ and $R_4$ comprises a substituted or unsubstituted alkyl group comprising at least six carbon atoms.

In one aspect, which is combinable with any of the other aspects or embodiments, X and Y are, independently, at least one unfused thiophene groups.

In one aspect, which is combinable with any of the other aspects or embodiments, p and q are different values.

In some embodiments, a polymer comprises a composition described herein, the polymer having a molecular weight in a range of 4000 Da to 180,000 Da.

In some embodiments, an organic thin film transistor (OTFT) comprises: a substrate; a gate electrode over the substrate; a gate dielectric layer over the substrate; a patterned source and drain layer over the gate dielectric layer; and an organic semiconductor layer over the gate dielectric layer, the organic semiconductor layer comprising a polymer described herein.

In some embodiments, a device comprises a compound described herein, configured in an electronic, optoelectronic, or nonlinear optical device.

In one aspect, which is combinable with any of the other aspects or embodiments, the device comprises a transistor (FET), a thin-film transistor (TFT), an organic light-emitting diode (OLED), an electro-optic (EO) device, a conductive material, a two photon mixing material, an organic semiconductor, a RFID tag, an electroluminescent device, or a photovoltaic and sensor device.

In some embodiments, a composition has a repeat unit of Formula 4, or a salt, isomer, or analog thereof:

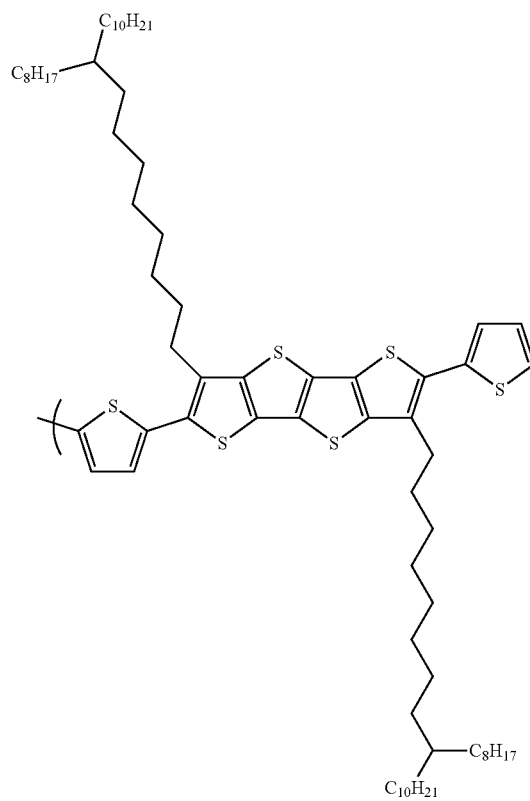

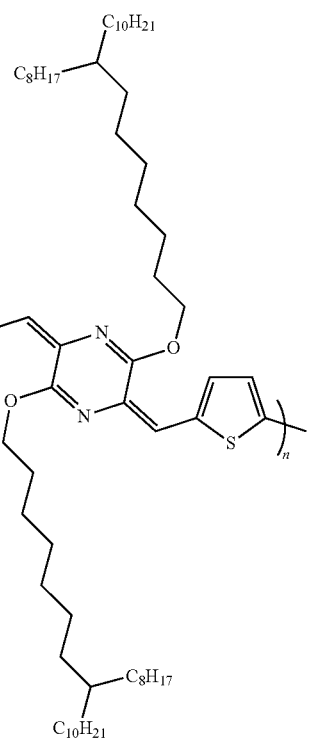

Formula 4 wherein n is an integer greater than or equal to one.

In some embodiments, a method of fabricating a dialkoxydimethylenedihydropyrazine (AMDHP) fused-thiophene (FT) organic semiconductor polymer, comprises: reacting tin-substituted dialkylated tetrathienoacene or thienyl-dialkylated tetrathienoacene with halogen-substituted thienyl-AMDHP; or reacting halogen-substituted dialkylated tetrathienoacene or thienyl-dialkylated tetrathienoacene with tin-substituted thienyl-AMDHP.

In one aspect, which is combinable with any of the other aspects or embodiments, the halogen-substituted dialkylated tetrathienoacene comprises:

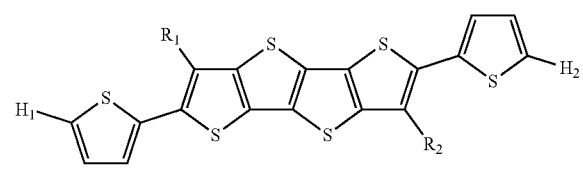

or a salt, isomer, or analog thereof, wherein $H_1$ and $H_2$ are, independently, chlorine (Cl), bromine (Br), and iodine (I), and wherein $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In one aspect, which is combinable with any of the other aspects or embodiments, at least one of $H_1$ and $H_2$ are Br.

In one aspect, which is combinable with any of the other aspects or embodiments, the tin-substituted dialkylated tetrathienoacene comprises:

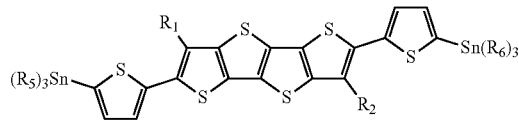

or a salt, isomer, or analog thereof, wherein $R_1$, $R_2$, $R_5$, and $R_6$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In one aspect, which is combinable with any of the other aspects or embodiments, at least one of $R_5$ and $R_6$ are substituted or unsubstituted alkyl groups.

In one aspect, which is combinable with any of the other aspects or embodiments, the thienyl-dialkylated tetrathienoacene comprises:

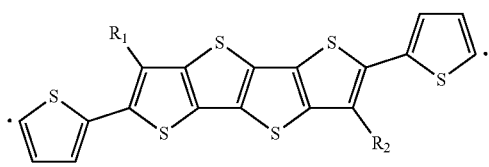

or a salt, isomer, or analog thereof, wherein $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In one aspect, which is combinable with any of the other aspects or embodiments, the halogen-substituted thienyl-AMDHP comprises:

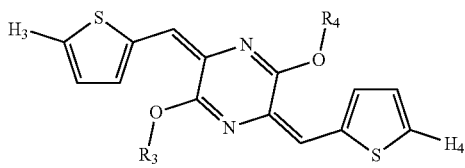

or a salt, isomer, or analog thereof, wherein $H_3$ and $H_4$ are, independently, chlorine (Cl), bromine (Br), and iodine (I), and wherein $R_3$ and $R_4$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In one aspect, which is combinable with any of the other aspects or embodiments, at least one of $H_3$ and $H_4$ are Br.

In one aspect, which is combinable with any of the other aspects or embodiments, the tin-substituted thienyl-AMDHP comprises:

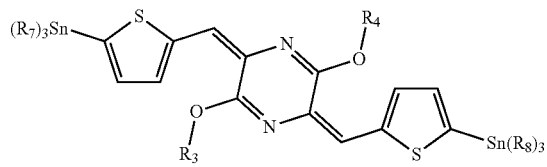

or a salt, isomer, or analog thereof, wherein $R_3$, $R_4$, $R_7$, and $R_8$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In one aspect, which is combinable with any of the other aspects or embodiments, at least one of $R_7$ and $R_8$ are substituted or unsubstituted alkyl groups.

BRIEF DESCRIPTION OF THE DRAWINGS

The disclosure will become more fully understood from the following detailed description, taken in conjunction with the accompanying FIGURES, in which:

FIGURE illustrates a plot of drain current as a function of gate voltage from an OTFT device prepared with dialkoxydimethylenedihydropyrazine (AMDHP) fused-thiophene (FT) organic semiconductor polymers, according to some embodiments.

DETAILED DESCRIPTION

Reference will now be made in detail to exemplary embodiments which are illustrated in the accompanying drawings. Whenever possible, the same reference numerals will be used throughout the drawings to refer to the same or like parts. The components in the drawings are not necessarily to scale, emphasis instead being placed upon illustrating the principles of the exemplary embodiments. It should be understood that the present application is not limited to the details or methodology set forth in the description or illustrated in the FIGURES. It should also be understood that the terminology is for the purpose of description only and should not be regarded as limiting.

Additionally, any examples set forth in this specification are illustrative, but not limiting, and merely set forth some of the many possible embodiments of the claimed invention. Other suitable modifications and adaptations of the variety of conditions and parameters normally encountered in the field, and which would be apparent to those skilled in the art, are within the spirit and scope of the disclosure.

DEFINITIONS

The term "alkyl group" refers to a monoradical branched or unbranched saturated hydrocarbon chain having 1 to 40 carbon atoms. This term is exemplified by groups such as methyl, ethyl, n-propyl, isopropyl, n-butyl, isobutyl, t-butyl, pentyl, n-hexyl, n-heptyl, n-octyl, n-decyl, or tetradecyl, and the like. The alkyl group can be substituted or unsubstituted.

The term "substituted alkyl group" refers to: (1) an alkyl group as defined above, having 1, 2, 3, 4 or 5 substituents, typically 1 to 3 substituents, selected from the group consisting of alkenyl, alkynyl, alkoxy, aralkyl, aldehyde, cycloalkyl, cycloalkenyl, acyl, acylamino, acyl halide, acyloxy, amino, aminocarbonyl, alkoxycarbonylamino, azido, cyano, halogen, hydroxy, keto, thiocarbonyl, carboxy, carboxyalkyl, arylthiol, ester, heteroarylthio, heterocyclylthio, hydroxyl, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl, thioalkyl, vinyl ether. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R$_{SO}$, where R$_{SO}$ is alkyl, aryl, or heteroaryl and n is 0, 1 or 2; or (2) an alkyl group as defined above that is interrupted by 1-10 atoms independently chosen from oxygen, sulfur and NR$_a$, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —S(O)$_n$R$_{SO}$, in which R$_{SO}$ is alkyl, aryl, or heteroaryl and n is 0, 1 or 2; or (3) an alkyl group as defined above that has both 1, 2, 3, 4 or 5 substituents as defined above and is also interrupted by 1-10 atoms as defined above. For example, the alkyl groups can be an alkyl hydroxy group, where any of the hydrogen atoms of the alkyl group are substituted with a hydroxyl group.

The term "alkyl group" as defined herein also includes cycloalkyl groups. The term "cycloalkyl group" as used herein is a non-aromatic carbon-based ring (i.e., carbocyclic) composed of at least three carbon atoms, and in some embodiments from three to 20 carbon atoms, having a single cyclic ring or multiple condensed rings. Examples of single ring cycloalkyl groups include, but are not limited to, cyclopropyl, cyclobutyl, cyclopentyl, cyclohexyl, cyclooctyl, and the like. Examples of multiple ring cycloalkyl groups include, but are not limited to, adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like. The term cycloalkyl group also includes a heterocycloalkyl group, where at least one of the carbon atoms of the ring is substituted with a heteroatom such as, but not limited to, nitrogen, oxygen, sulfur, or phosphorus.

The term "unsubstituted alkyl group" is defined herein as an alkyl group composed of just carbon and hydrogen.

The term "acyl" denotes a group —C(O)$R_{CO}$, in which $R_{CO}$ is hydrogen, optionally substituted alkyl, optionally substituted cycloalkyl, optionally substituted heterocyclyl, optionally substituted aryl, and optionally substituted heteroaryl.

The term "aryl group" as used herein is any carbon-based aromatic group (i.e., aromatic carbocyclic) such as having a single ring (e.g., phenyl) or multiple rings (e.g., biphenyl), or multiple condensed (fused) rings (e.g., naphthyl or anthryl). These may include, but are not limited to, benzene, naphthalene, phenyl, etc.

The term "aryl group" also includes "heteroaryl group," meaning a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen, sulfur, and phosphorus within at least one ring. In other words, heteroaryl groups are aromatic rings composed of at least three carbon atoms that has at least one heteroatom incorporated within the ring of the aromatic group. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, triazole, oxazole, thiazole, naphthyridine, and the like as well as N-oxide and N-alkoxy derivatives of nitrogen containing heteroaryl compounds, for example pyridine-N-oxide derivatives.

Unless otherwise constrained by the definition for the heteroaryl substituent, such heteroaryl groups can be optionally substituted with 1 to 5 substituents, typically 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The aryl group can be substituted or unsubstituted. Unless otherwise constrained by the definition for the aryl substituent, such aryl groups can optionally be substituted with from 1 to 5 substituents, typically 1 to 3 substituents, selected from the group consisting of alkyl, alkenyl, alkynyl, alkoxy, aldehyde, cycloalkyl, cycloalkenyl, acyl, acylamino, acyloxy, amino, aminocarbonyl, alkoxycarbonylamino, azido, cyano, ester, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2. In some embodiments, the term "aryl group" is limited to substituted or unsubstituted aryl and heteroaryl rings having from three to 30 carbon atoms.

The term "aralkyl group" as used herein is an aryl group having an alkyl group or an alkylene group as defined herein covalently attached to the aryl group. An example of an aralkyl group is a benzyl group. "Optionally substituted aralkyl" refers to an optionally substituted aryl group covalently linked to an optionally substituted alkyl group or alkylene group. Such aralkyl groups are exemplified by benzyl, phenylethyl, 3-(4-methoxyphenyl)propyl, and the like.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "alkenyl group" refers to a monoradical of a branched or unbranched unsaturated hydrocarbon group typically having from 2 to 40 carbon atoms, more typically 2 to 10 carbon atoms and even more typically 2 to 6 carbon atoms and having 1-6, typically 1, double bond (vinyl). Typical alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. When alkenyl is attached to nitrogen, the double bond cannot be alpha to the nitrogen.

The term "substituted alkenyl group" refers to an alkenyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "cycloalkenyl group" refers to carbocyclic groups of from 3 to 20 carbon atoms having a single cyclic ring or multiple condensed rings with at least one double bond in the ring structure.

The term "alkynyl group" refers to a monoradical of an unsaturated hydrocarbon, typically having from 2 to 40 carbon atoms, more typically 2 to 10 carbon atoms and even more typically 2 to 6 carbon atoms and having at least 1 and typically from 1-6 sites of acetylene (triple bond) unsaturation. Typical alkynyl groups include ethynyl, (—C≡CH), propargyl (or prop-1-yn-3-yl, —CH$_2$C≡CH), and the like. When alkynyl is attached to nitrogen, the triple bond cannot be alpha to the nitrogen.

The term "substituted alkynyl group" refers to an alkynyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "alkylene group" is defined as a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, typically 1-10 carbon atoms, more typically 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene group" refers to: (1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2; or (2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocyclyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), and the like.

The term "alkoxy group" refers to the group R—O—, where R is an optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio group" refers to the group R$_S$—S—, where R$_S$ is as defined for alkoxy.

The term "aminocarbonyl" refers to the group —C(O)NR$_N$R$_N$ where each R$_N$ is independently hydrogen, alkyl, aryl, heteroaryl, heterocyclyl or where both R$_N$ groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "acylamino" refers to the group —NR$_{NCO}$C(O)R where each R$_{NCO}$ is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "aryloxy group" refers to the group aryl-O— wherein the aryl group is as defined above, and includes optionally substituted aryl groups as also defined above.

The term "heteroaryloxy" refers to the group heteroaryl-O—.

The term "amino" refers to the group —NH$_2$.

The term "substituted amino" refers to the group —NR$_w$R$_w$ where each R$_w$ is independently selected from the group consisting of hydrogen, alkyl, cycloalkyl, carboxyalkyl (for example, benzyloxycarbonyl), aryl, heteroaryl and heterocyclyl provided that both R$_w$ groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "carboxy" refers to a group —C(O)OH. The term "carboxyalkyl group" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, and —S(O)$_n$R$_{SO}$, in which R$_{SO}$ is alkyl, aryl, or heteroaryl and n is 0, 1 or 2.

The terms "substituted cycloalkyl group" or "substituted cycloalkenyl group" refer to cycloalkyl or cycloalkenyl groups having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "conjugated group" is defined as a linear, branched or cyclic group, or combination thereof, in which p-orbitals of the atoms within the group are connected via delocalization of electrons and wherein the structure can be described as containing alternating single and double or triple bonds and may further contain lone pairs, radicals, or carbenium ions. Conjugated cyclic groups may comprise both aromatic and non-aromatic groups, and may comprise polycyclic or heterocyclic groups, such as diketopyrrolopyrrole. Ideally, conjugated groups are bound in such a way as to continue the conjugation between the thiophene moieties they connect. In embodiments, "conjugated groups" is limited to conjugated groups having three to 30 carbon atoms.

The term "halogen," "halo," or "halide" may be referred to interchangeably and refer to fluoro, bromo, chloro, and iodo.

The term "heterocyclyl" refers to a monoradical saturated or partially unsaturated group having a single ring or multiple condensed rings, having from 1 to 40 carbon atoms and from 1 to 10 hetero atoms, typically 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclyl substituent, such heterocyclyl groups can be optionally substituted with 1, 2, 3, 4 or 5, and typically 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "thiol" refers to the group —SH. The term "substituted alkylthio" refers to the group —S-substituted alkyl. The term "arylthiol group" refers to the group aryl-S—, where aryl is as defined as above. The term "heteroarylthiol" refers to the group —S-heteroaryl wherein the heteroaryl group is as defined above including optionally substituted heteroaryl groups as also defined above.

The term "sulfoxide" refers to a group —S(O)R$_{SO}$, in which R$_{SO}$ is alkyl, aryl, or heteroaryl. The term "substituted sulfoxide" refers to a group —S(O)R$_{SO}$, in which R$_{SO}$ is substituted alkyl, substituted aryl, or substituted heteroaryl, as defined herein. The term "sulfone" refers to a group —S(O)$_2$R$_{SO}$, in which R$_{SO}$ is alkyl, aryl, or heteroaryl. The term "substituted sulfone" refers to a group —S(O)$_2$R$_{SO}$, in which R$_{SO}$ is substituted alkyl, substituted aryl, or substituted heteroaryl, as defined herein.

The term "keto" refers to a group —C(O)—. The term "thiocarbonyl" refers to a group —C(S)—.

As used herein, the term "room temperature" is 20° C. to 25° C.

Disclosed are compounds, compositions, and components that can be used for, can be used in conjunction with, can be used in preparation of, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A weight percent of a component, unless specifically stated to the contrary, is based on the total weight of the formulation or composition in which the component is included.

Organic semiconductors as functional materials may be used in a variety of applications including, for example, printed electronics, organic transistors, including organic thin-film transistors (OTFTs) and organic field-effect transistors (OFETs), organic light-emitting diodes (OLEDs), organic integrated circuits, organic solar cells, and disposable sensors. Organic transistors may be used in many applications, including smart cards, security tags, and the backplanes of flat panel displays. Organic semiconductors may substantially reduce cost compared to inorganic counterparts, such as silicon. Depositing OSCs from solution may enable fast, large-area fabrication routes such various printing methods and roll-to-roll processes.

As stated above, performances of devices comprising organic semiconductor materials may be evaluated by charge carrier mobility, current on/off ratio, threshold voltage, and magnitude of the on/off current. The ability to achieve high electrical parameters from solution deposition processes with minimal processing steps is a strong advantage. Thus, it is necessary to prepare stable inks or formulations of the polymeric semiconducting materials. The present disclosure provides a new combination of fused thiophenes with dialkoxydimethylenedihydropyrazine (AMDHP) (shown below in Formula 1, where the dashed lines indicate connection points to other portions of a polymer chain).

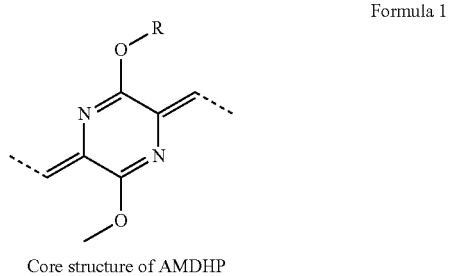

Core structure of AMDHP

Specifically, this new class of fused thiophene-based semiconducting polymers employs a new high-efficiency electron acceptor (AMDHP) having high conjugation and good solubility in organic solvents. Generic polymeric structures of the composition comprising a AMDHP fused-thiophene organic semiconductor polymer having a repeat unit of Formula 2 or Formula 3, or a salt, isomer, or analog thereof, are shown below.

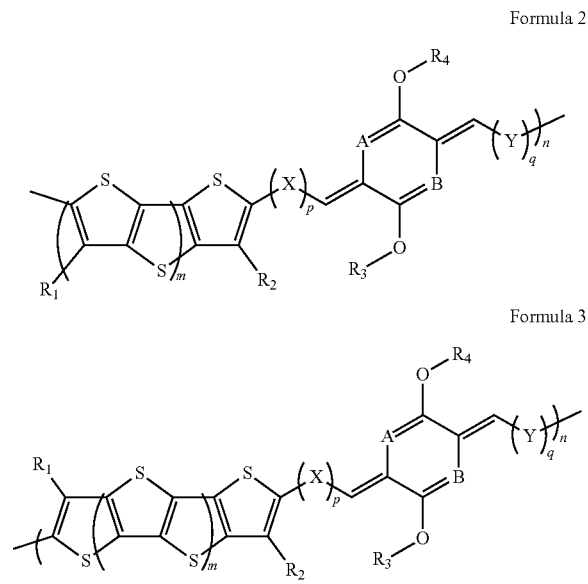

where m is an integer greater than or equal to zero; wherein n is an integer greater than or equal to one; X and Y are, independently, a covalent bond or aryl; A and B are, independently, a nitrogen group or a C—H group; $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted; $R_3$ and $R_4$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted; and p and q are, independently, integers greater than or equal to zero. In some examples, isomers of Formulas 2 and 3 include the [E,Z], [E,E], [Z,Z], or [Z,E] configurations of the double bonds connected to the AMDHP ring structure, as shown in Formula 1.

As used herein, the fused thiophene ring system of a fused thiophene moiety is the heterocyclic core of the moiety, and does not include the a-substituents and the β-substituents (e.g. $R_1$ and $R_2$) bound to the fused thiophene ring system. In some examples, any of the sulfur atoms present in the fused thiophene compounds described herein can be oxidized to produce a $SO_2$ group. The fused thiophene moieties described herein can have any number of fused rings, for example, m may be 1, 2, 3, 4, 5, 6, 7, 8, 9, 10, 11, 12, 13, 14, or 15. In some examples, the fused thiophene moieties described herein are substituted at least one of the β-positions of the fused thiophene ring system with an alkyl group. As used herein, an α-position of a fused thiophene ring system is a non-fused carbon center that is directly adjacent to the sulfur of a fused thiophene, while a β-position is a non-fused carbon center that is separated from the sulfur of the fused thiophene by an α-position. In Formulas 2 and 3, the α-positions are shown as being connected to the rest of the composition, while the β-positions are substituted with $R_1$ and $R_2$.

In some examples, A is nitrogen and B is a C—H group. In some examples, A is a C—H group and B is nitrogen. In some examples, A is nitrogen and B is nitrogen. In some examples, A is a C—H group and B is a C—H group.

In some examples, $R_1$ and/or $R_2$ may be a variety of substituted or unsubstituted alkyl groups. For example, at least one of $R_1$ or $R_2$ is an unsubstituted alkyl group. In this aspect, the unsubstituted alkyl group can be a straight-chain alkyl group (e.g. methyl, ethyl, propyl, butyl, pentyl, hexyl, heptyl, octyl, nonyl, decyl, undecyl, dodecyl or hexadecyl), a branched alkyl group (e.g. sec-butyl, neo-pentyl, 4-methylpentyl), or a substituted or unsubstituted cycloalkyl group (e.g. cyclopentyl, cyclohexyl). In another aspect, at least one of $R_1$ or $R_2$ is an alkyl group, itself at least four carbons in size, which is substituted. In another aspect, substitution of the alkyl group is separated from the fused thiophene ring system by at least two carbons. In some examples, $R_1$ and/or $R_2$ can be substituted with an aryl group, cycloalkyl group, aralkyl group, an alkenyl group, an alkynyl group, an amino group, an ester, an aldehyde, a hydroxyl group, an alkoxy group, a thiol group, a thioalkyl group, or a halide, acyl halide, an acrylate, a vinyl ether, or in combination thereof. Examples of substituted alkyl groups include, but are not limited to, 6-hydroxyhexyl and 3-phenylbutyl. The selection of $R_1$ and $R_2$ depend on the end use of the fused thiophene moiety-containing composition. The methods described herein permit the synthesis of fused thiophene moieties having a wide variety of $R_1$ and $R_2$ substituents. Any functionality on a substituted alkyl group can be protected in order to survive subsequent reaction steps.

Unsubstituted fused thiophene ring systems (i.e., no substitution at the α- or β-positions) tend to be relatively insoluble. Thus, in one aspect, $R_1$ and $R_2$ can be an alkyl group having at least six carbons in size. For example, the alkyl group can have the formula $C_kH_{2k+1}$, where k is an integer greater than or equal to six.

In some examples, $R_1$ and $R_2$ may be any species except hydrogen and may be independently chosen to be the same as or different from each other. In other words, the fused thiophene ring system is substituted at both β-positions, such that there are no β-hydrogens on the ring system (i.e., neither $R_1$ nor $R_2$ in Formulas 2 or 3 is H). Such moieties can be incorporated in oligomers and polymers having substantially no β-hydrogen content, and will have increased oxidative stability. For example, the molar ratio of β-hydrogen to fused thiophene ring system can be less than about 1:6, 1:7, 1:8, 1:9, or 1:10. In some examples, one or both of $R_1$ and $R_2$ can be an alkyl group. In one aspect, $R_1$ and $R_2$ are identical alkyl groups. When $R_1$ and $R_2$ are identical, regioregular polymers may be easily constructed because the problems of regioselectivity (i.e. head-to-tail vs. head-to-head coupling) of polymerization reactions disappear. In some examples, $R_1$ and $R_2$ may be different. For example, $R_1$ can be at least four carbons in size, with $R_2$ being less than four carbons in size (e.g., a methyl group). Alternatively, in other examples, both $R_1$ and $R_2$ may be at least four carbons in size.

In some examples, $R_3$ and $R_4$ may be a variety of substituted or unsubstituted alkyl groups as described above for $R_1$ and $R_2$. For example, the unsubstituted alkyl group can be a straight-chain alkyl group (e.g. methyl, ethyl, propyl, butyl, pentyl, hexyl, heptyl, octyl, nonyl, decyl, undecyl, dodecyl or hexadecyl), a branched alkyl group (e.g. sec-butyl, neopentyl, 4-methylpentyl), or a substituted or unsubstituted cycloalkyl group (e.g. cyclopentyl, cyclohexyl). In other examples, $R_3$ and/or $R_4$ can be substituted with an aryl group, cycloalkyl group, aralkyl group, an alkenyl group, an alkynyl group, an amino group, an ester, an aldehyde, a hydroxyl group, an alkoxy group, a thiol group, a thioalkyl group, or a halide, acyl halide, an acrylate, a vinyl ether, or in combination thereof. Moreover, in some examples, $R_3$ and $R_4$ may be any species except hydrogen and may be independently chosen to be the same as or different from each other. In some examples, at least one of $R_3$ and $R_4$ comprises a substituted or unsubstituted alkyl group comprising at least six carbon atoms.

In some examples, p is an integer greater than or equal to two and q is an integer greater than or equal to one. In some examples, p and/or q are equal to zero.

X and Y are conjugated groups that are connected to the AMDHP and fused thiophene moieties to provide one or more continuous conjugated pathways along the polymer backbone. In some examples, X is the same as Y. In some examples, X is different from Y. In some examples, X, Y, or X and Y are non-existent (i.e., p and/or q are equal to zero) such that there is a direct connection between the fused thiophene and the AMDHP moiety. In some examples, X and Y are, independently, at least one unfused thiophene groups.

In some examples, the AMDHP fused-thiophene organic semiconductor polymer having a repeat unit of Formula 2 or Formula 3 has a molecular weight in a range of 4000 Daltons (Da) to 180,000 Da, or in a range of 10,000 Da to 150,000 Da, or in a range of 20,000 Da to 130,000 Da, or in a range of 40,000 Da to 120,000 Da, or in a range of 50,000 Da to 125,000 Da, or in a range of 75,000 Da to 100,000 Da.

In some examples, the molecular weight of the polymers having conjugated homo-monomeric (i.e., single), homo-oligomeric, or homopolymeric blocks of the Formula 2 or Formula 3 moieties have molecular weights from about 4,000 to about 180,000, about 4,000 to about 160,000, about 4,000 to about 140,000, about 4,000 to about 120,000, about 4,000 to about 100,000, about 4,000 to about 80,000, about 4,000 to about 70,000, about 4,000 to about 60,000, about 4,000 to about 50,000, about 4,000 to about 40,000, about 4,000 to about 30,000, about 5,000 to about 180,000, about 5,000 to about 160,000, about 5,000 to about 140,000, about 5,000 to about 120,000, about 5,000 to about 100,000, about 5,000 to about 80,000, about 5,000 to about 70,000, about 5,000 to about 60,000, about 5,000 to about 50,000, about 5,000 to about 40,000, about 5,000 to about 30,000, about 10,000 to about 180,000, about 10,000 to about 160,000, about 10,000 to about 140,000, about 10,000 to about 120,000, about 10,000 to about 100,000, about 10,000 to about 80,000, about 10,000 to about 70,000, about 10,000 to about 60,000, about 10,000 to about 50,000, about 10,000 to about 40,000, about 10,000 to about 30,000, about 20,000 to about 180,000, about 20,000 to about 160,000, about 20,000 to about 140,000, about 20,000 to about 120,000, about 20,000 to about 100,000, about 20,000 to about 80,000, about 20,000 to about 70,000, about 20,000 to about 60,000, about 20,000 to about 50,000, about 20,000 to about 40,000, about 20,000 to about 30,000, about 30,000 to about 180,000, about 30,000 to about 160,000, about 30,000 to about 140,000, about 30,000 to about 100,000, about 30,000 to about 80,000, about 30,000 to about 70,000, about 30,000 to about 60,000, about 30,000 to about 50,000, about 30,000 to about 40,000, about 50,000 to about 180,000, about 50,000 to about 160,000, about 50,000 to about 140,000, about 50,000 to about 120,000, about 50,000 to about 100,000, about 50,000 to about 80,000, about 50,000 to about 70,000, or about 50,000 to about 60,000 Da.

In some examples, the molecular weight of the polymers having conjugated homo-monomeric (i.e., single), homo-oligomeric, or homopolymeric blocks of the Formula 2 or Formula 3 moieties have molecular weights of about 3000, 4000, 5000, 6000, 7000, 8000, 9000, 10,000, 15,000, 20,000, 25,000, 30,000, 40,000, 50,000, 60,000, 70,000, 80,000, 90,000, 100,000, 110,000, 120,000, 130,000, 140,000 150,000, 160,000, 170,000, or 180,000 Da.

In some examples, the AMDHP fused-thiophene organic semiconductor polymer has a repeat unit of Formula 4, or a salt, isomer, or analog thereof, as shown below.

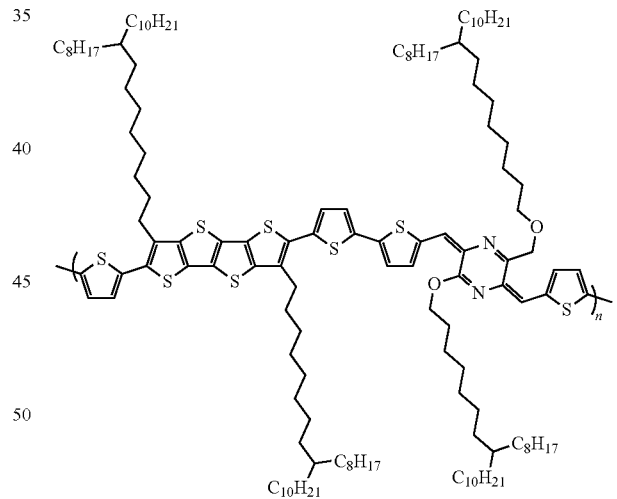

Formula 4 wherein n is an integer greater than or equal to one.

Described herein are methods for making fused thiophene-based semiconducting polymers employing dialkoxydimethylenedihydropyrazine (AMDHP) group electron acceptors.

In some examples, a method of fabricating a dialkoxydimethylenedihydropyrazine (AMDHP) fused-thiophene (FT) organic semiconductor polymer by Stille coupling includes reacting tin-substituted dialkylated tetrathienoacene or thienyl-dialkylated tetrathienoacene with halogen-substituted thienyl-AMDHP; or reacting halogen-substituted dialkylated tetrathienoacene or thienyl-dialkylated tetrathienoacene with tin-substituted thienyl-AMDHP.

In some examples, the halogen-substituted dialkylated tetrathienoacene comprises a structure of Formula 5, or a salt, isomer, or analog thereof:

Formula 5

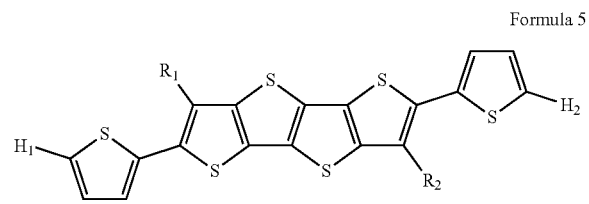

wherein $H_1$ and $H_2$ are, independently, chlorine (Cl), bromine (Br), and iodine (I), and wherein $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether or in combination thereof, with each of the preceeding being substituted or unsubstituted.

In some examples, the tin-substituted dialkylated tetrathienoacene comprises a structure of Formula 6, or a salt, isomer, or analog thereof:

Formula 6

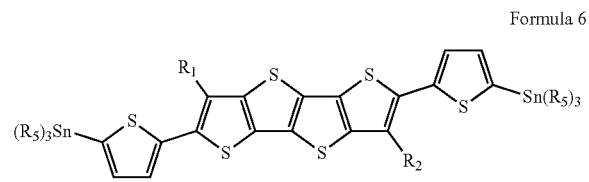

wherein $R_1$, $R_2$, $R_5$, and $R_6$ are, independently, substituted or unsubstituted alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In some examples, the thienyl-dialkylated tetrathienoacene comprises a structure of Formula 7, or a salt, isomer, or analog thereof:

Formula 7

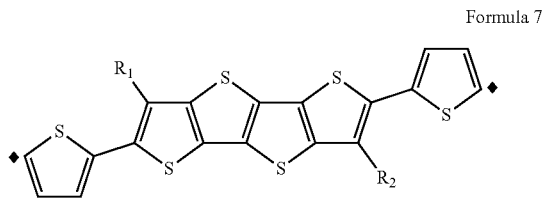

wherein $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In some examples, the halogen-substituted thienyl-AMDHP comprises a structure of Formula 8, or a salt, isomer, or analog thereof:

Formula 8

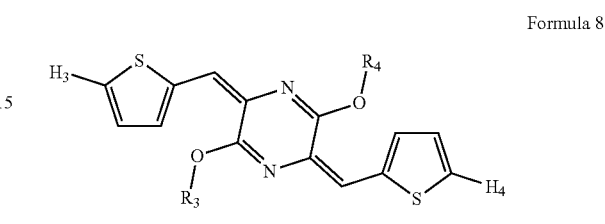

wherein $H_3$ and $H_4$ are, independently, chlorine (Cl), bromine (Br), and iodine (I), and wherein $R_3$ and $R_4$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In some examples, the tin-substituted thienyl-AMDHP comprises a structure of Formula 9, or a salt, isomer, or analog thereof:

Formula 9

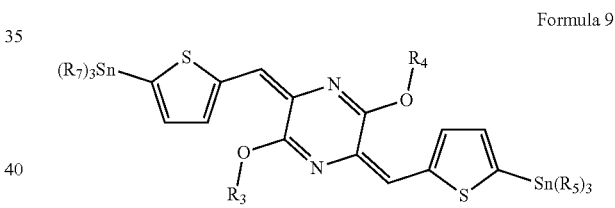

wherein $R_3$, $R_4$, $R_7$, and $R_8$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or in combination thereof, with each of the preceeding being substituted or unsubstituted.

In some examples, Stille coupling by reacting tin-substituted dialkylated tetrathienoacene with halogen-substituted thienyl-AMDHP is shown in Reaction Scheme 1:

Reaction Scheme 1

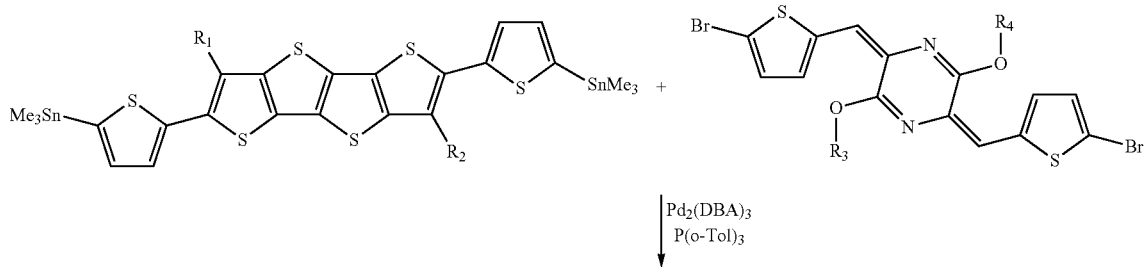

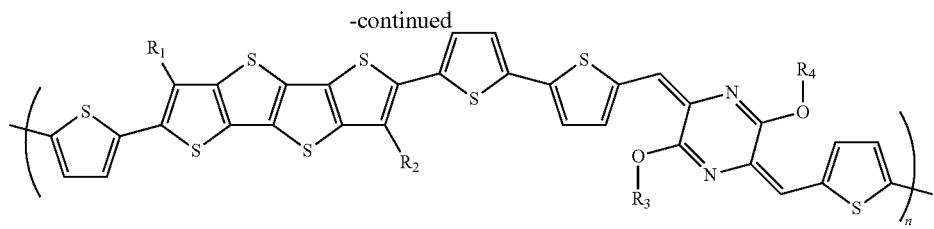

In some examples, Stille coupling by reacting halogen-substituted dialkylated tetrathienoacene with tin-substituted thienyl-AMDHP is shown in Reaction Scheme 2:

Reaction Scheme 2

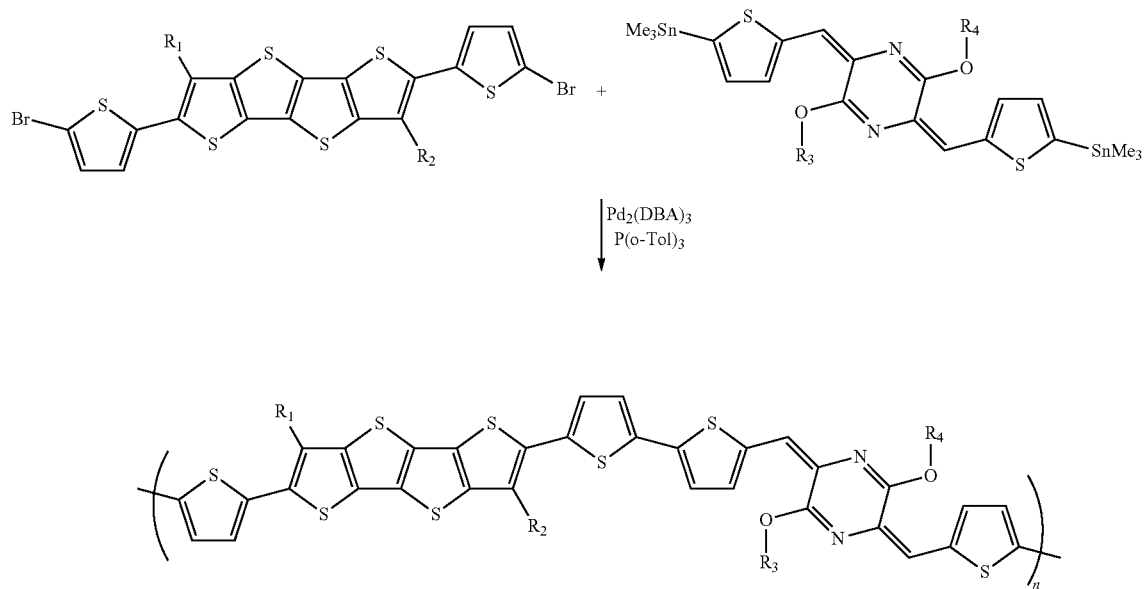

In some examples, isomers of the final compound in Reaction Scheme 2 may be formed and include the [E,Z], [E,E], [Z,Z], or [Z,E] configurations of the double bonds connected to the AMDHP ring structure.

EXAMPLES

The embodiments described herein will be further clarified by the following examples.

Example 1

Preparation of AMDHP Fused-Thiophene Organic Semiconductor Polymer

The synthesis of the compound of Formula 4 was prepared according to Reaction Scheme 3 (shown below) where a tin-substituted dialkylated tetrathienoacene was reacted with a halogen-substituted thienyl-AMDHP.

Reaction Scheme 3

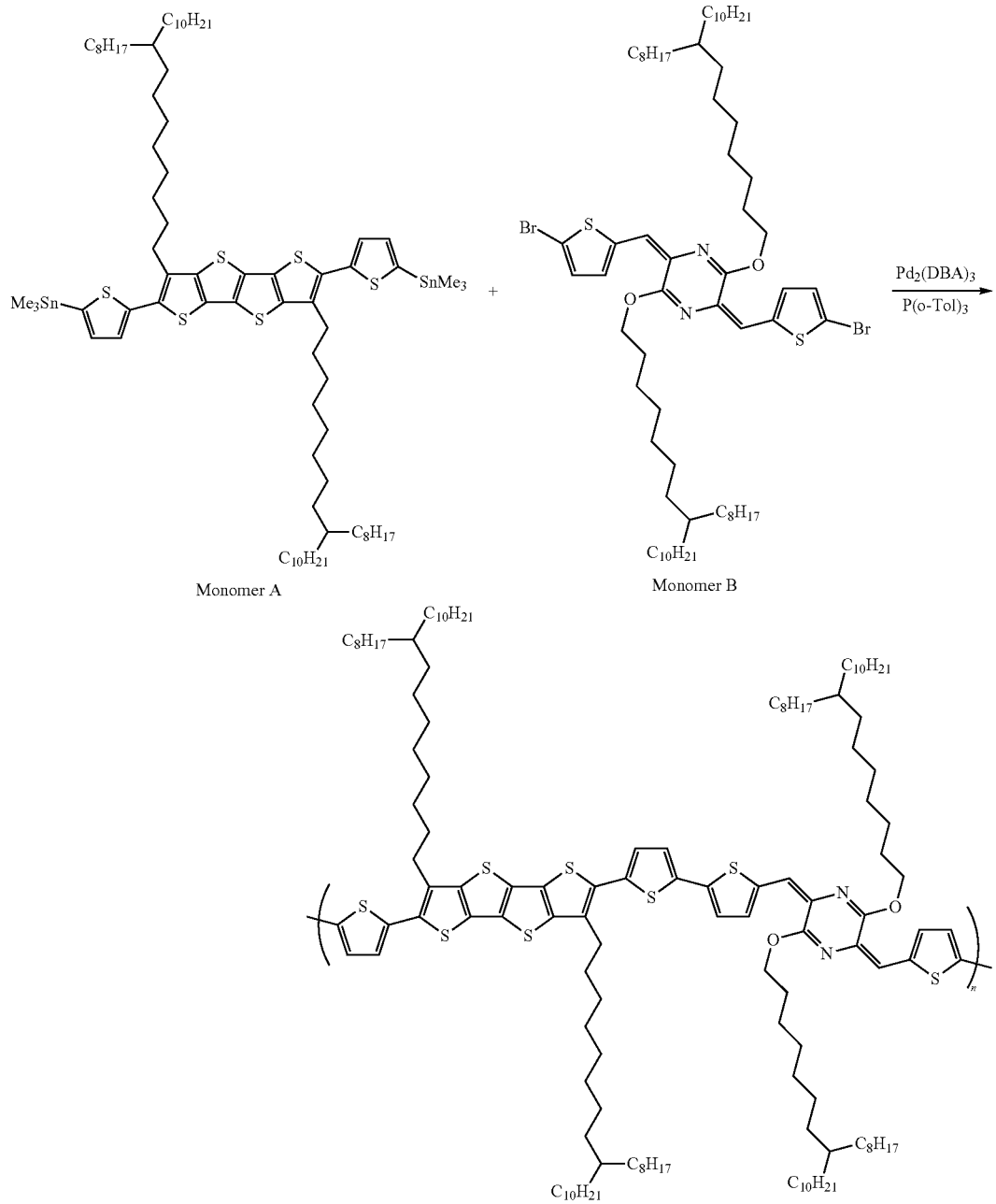

Monomer A (tin-substituted-thienyl dialkylated tetrathienoacene) was synthesized using the following procedure. To a 100 mL flask, DTh Branched FT4 (2.3 g, 2.0 mmol, 1.0 eq.) and DCM (25 mL) were added under nitrogen protection. The reaction solution was cooled to 0° C. to 5° C. N-Bromosuccinimide (NBS) (0.72 g, 4.04 mmol, 2.02 eq.) was added in several small portions into the flask making sure that the reaction solution stayed below 10° C. The reaction mixture was stirred for 2 hrs below 10° C. HPLC analysis confirmed the completed reaction. Methylene chloride was removed under reduced pressure at 30° C. Hexane (20 mL) was added, and the resulting slurry was passed through a silica gel column eluting with hexane. The hexane was evaporated under reduced pressure to give the desired DBrTh Branched FT4 (2.46 g, 96.4% yield, 96.2% HPLC purity) after drying under vacuum. $^1$H NMR (400 MHz, CDCl$_3$, ppm) δ=7.06 (d, 2H), 6.93 (d, 2H), 2.88 (t, 4H), 1.77 (p, 4H), 1.52-1.00 (m, 92H), 0.93-0.76 (m, 12H).

Thereafter, in a three-neck flask at −78° C. and under nitrogen protection, n-BuLi (2.0 M in hexane (18.02 mL, 36.04 mmol) was added dropwise by syringe. The resulting solution was stirred at −78° C. for 4 hrs. The reaction temperature was then warmed to −12° C. and solid trimethyltinchloride (14.96 g, 75.08 mmol) was added under nitrogen protection. The reaction solution was warmed to room temperature and stirred overnight. This reaction solution was quenched by adding ice-water. After removing most of the THF under reduced pressure, 300 mL of water and 300 mL of hexane were added. After vigorously shaking, the hexane layer was collected, washed by water and then dried over anhydrous sodium sulfate. After filtration, the hexane was removed under reduced pressure to yield an oily product. To this oily product, 90 mL of hot (~50° C.) anhydrous acetone was added and the mixture swirled. The acetone was then decanted while hot and the resulting oily product was dried under vacuum to yield monomer A (9.80 g, 91% yield). $^1$H NMR (400 MHz, CDCl$_3$, ppm) δ=7.29 (d, 2H), 7.17 (d, 2H), 2.93 (t, 4H), 1.77 (p, 4H), 1.49-1.10 (m, 92H), 0.92-0.79 (m, 12H), 0.42 (s, 18H). Reaction Scheme 4 summarizes the synthesis procedure of Monomer A.

Reaction Scheme 4

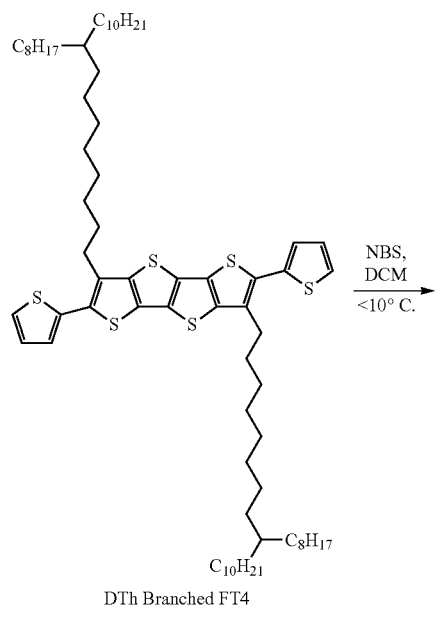

DTh Branched FT4

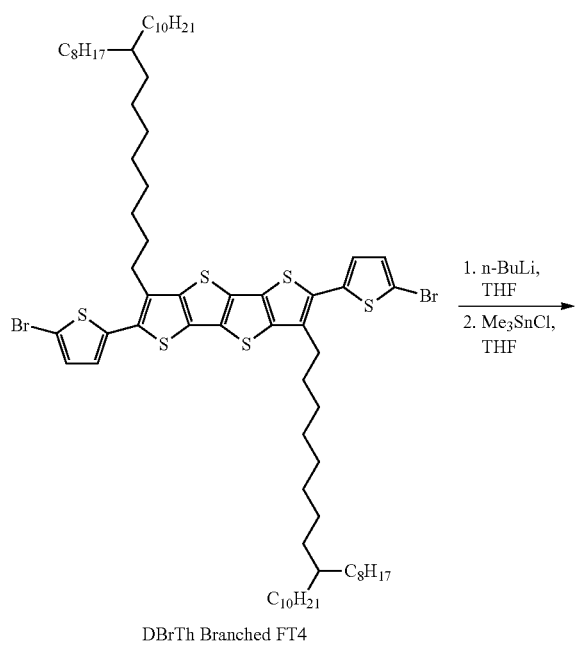

DBrTh Branched FT4

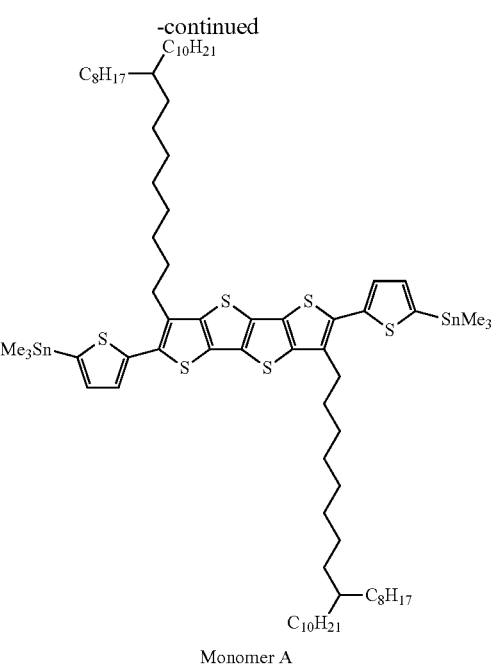

Monomer A

Monomer B (halogen-substituted thienyl-AMDHP) was synthesized using the following procedure. Under nitrogen protection, 1.20 g (2.61 mmol) of bromothienyl-MPD, 2.99 g (15.65 mmol) of anhydrous potassium carbonate, 5.81 g (13.04 mmol) of 9-(7-bromoheptyl)nonadecane, and 25 mL of anhydrous DMF were added to a 100 mL round-bottom flask with a condenser and a stir bar. The resulting mixture was stirred and heated at 100° C. for two hours. After cooling to room temperature, the potassium carbonate solid was removed by filtration and the filtrate was concentrated by rotary evaporation under reduced press to remove DMF solvent. The residue was subject to column chromatography (using hexane/CHCl$_3$ changing from 9:1 to 4:1 volume ratios) to afford the desired product as a red solid. Fifty milliliters of hexane was added to this redish solid product and this mixture was stirred at 50° C. in a water bath to form a translucent solution that was kept in the refrigerator overnight to form a dark redish precipitate. The precipitate was collected by filtration and dried under vacuum to give the product (monomer B, bromothienyl-DC8BC8C10AMDHP (19% yield, 0.731 g, 0.488 mmol, MW 1499.96)). $^1$H NMR (300 MHz, CD$_2$Cl$_2$): 7.12 (s, 2H), 7.09-7.04 (m, 4H), 4.52 t, 4H), 1.93 (p, 4H), 1.63-1.19 (m, 82H), 0.95-0.85 (m, 16H). Reaction Scheme 5 summarizes the synthesis procedure of Monomer B.

Reaction Scheme 5
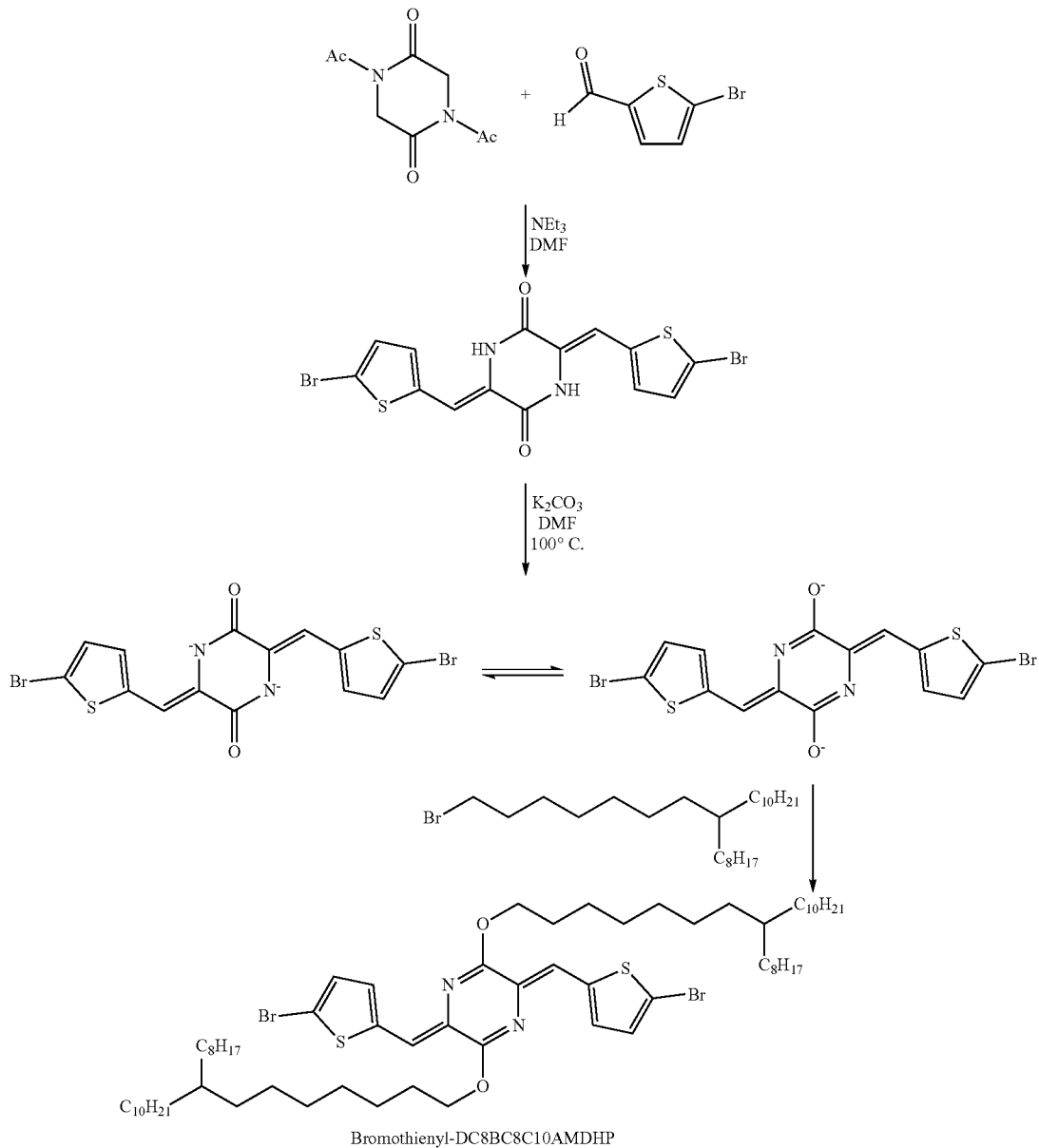
In addition to the [Z,Z] isomer formed after the first reaction step of Reaction Scheme 5, each of the following isomeric configurations may or may not be formed as well, with Reaction Scheme 5 proceeding analogously as defined above:
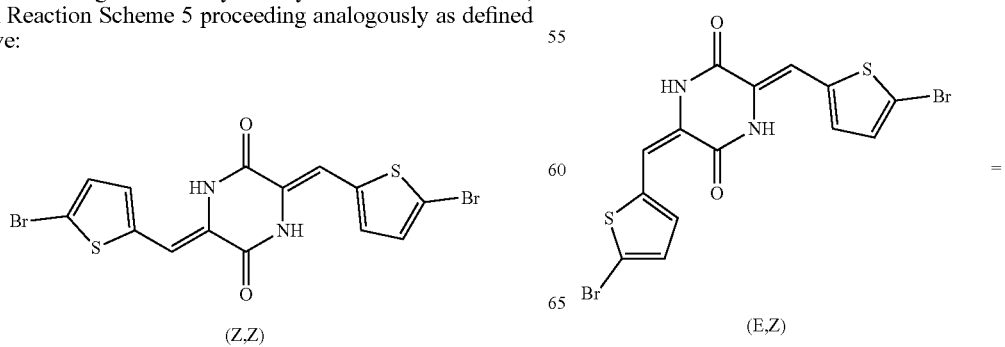

-continued

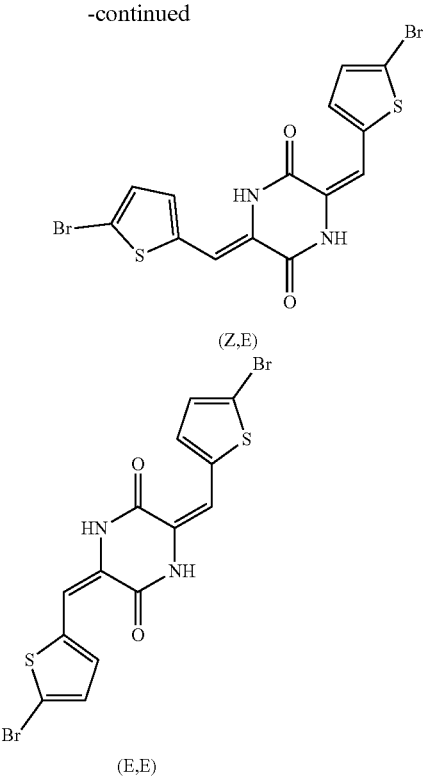

(Z,E)

(E,E)

Thus, Monomer B may be formed from at least one or a combination of the [Z,Z], [E,Z], [Z,E], and [E,E] isomers.

Thereafter, Monomer A 0.731 g (0.488 mmol, MW 1499.96), monomer B 0.58 g (0.488 mmol), and catalyst tris(dibenzylideneacetone)dipalladium(0) 8.94 mg (0.0098 mmol) with o-tolyl phosphine 11.9 mg (0.039 mmol) were weighted into a round bottom flask (100 mL). Chlorobenzene (22 mL) and a stir bar were added. A condenser was fitted and the reaction mixture was lowered into an oil bath pre-heated to 125° C. and heated under nitrogen for 1 hr. The mixture was then poured into a stirring mixture of methanol and acetylacetone (200 mL+200 mL). Hydrochloric acid (2 mL, 35% aq) was added and the mixture stirred for 16 hrs. The mixture was then precipitated, filtered, dried, and then the polymer was placed into a soxhlet thimble to remove any residual monomers and catalyst species. The polymer was extracted in a soxhlet apparatus with acetone (250 mL) for 24 hrs., then hexanes (250 mL) for 24 hrs. The polymer was then extracted from the soxhlet apparatus into chloroform (250 mL). The chloroform solution was poured into acetone (400 mL) with rapid stirring, followed by moderate stirring for 20 min. The polymer was then filtered from the mixture and dried under vacuum to give the product as a purple solid (0.90 g, 84% yield) (see Reaction Scheme 3).

The molecular weights referred to herein for organic semiconductor polymers are number average molecular weights determined by gel permeation chromatography (GPC) (Agilent GPC220®) run at 200° C. with 1,2,4-trichlorobenzene as the mobile phase with a flow rate of 1 mL/min, and referenced to polystyrene standards. The column used was a Resipore 300×7.5 mm column. A refractive index detector, previously calibrated against polystyrene standards in the range 10,000 to 240,000, was used to determine the molecular weights, as shown in Table 1. Unless otherwise specified, molecular weights referred to herein are number average molecular weights (Mn).

The polydispersity index (PDI, Mw/Mn) is a measure of the distribution of molecular mass in a given polymer sample. Mn is more sensitive to molecules of low molecular mass, while Mw is more sensitive to molecules of high molecular mass. The dispersity indicates the distribution of individual molecular masses in a batch of polymers. PDI has a value equal to or greater than one, however, as the polymer chains approach uniform chain length, PDI approaches unity.

TABLE 1

| Number Avg. Molecular Wt. (Mn) | Wt. Avg. Molecular Wt. (Mw) | Polydispersity Index (PDI) |
|---|---|---|
| 35,500 | 80,400 | 2.26 |

Example 2

Preparation of Devices with AMDHP Fused-Thiophene Organic Semiconductor Polymer

In some examples, a device having the AMDHP fused-thiophene organic semiconductor polymer described herein may be an electronic, optoelectronic, or nonlinear optical device, such as field-effect transistors (FET), thin-film transistors (TFT), organic light-emitting diodes (OLED), electro-optic (EO) devices, conductive materials, two photon mixing materials, organic semiconductors, RFID tags, electroluminescent devices, or photovoltaic and sensor devices.

In some examples, an organic thin film transistor (OTFT) includes a substrate; a gate electrode over the substrate; a gate dielectric layer over the substrate; a patterned source and drain layer over the gate dielectric layer; an organic semiconductor (OSC) layer over the gate dielectric layer; and, optionally, an insulator layer over the patterned source and drain layer, such that the OSC layer comprises the polymer having the composition of Formulas 2 or 3 (e.g., Formula 4). Specifically, the OTFT may have a bottom gate, top contact configuration, with a silicon gate and an octadecyltrimethoxylsilyl-treated thermal oxide silica dielectric layer. Other configurations of the OTFT are contemplated that produce fully functional devices. For example, the gate and/or source and drain may be, independently, positioned above or below the OSC layer.

Table 2 shows performance data for devices having a 50 nm thick OSC layer of the polymer composition of Formula 4; Table 3 shows performance data for devices having a 35 nm thick OSC layer of the polymer composition of Formula 4.

TABLE 2

| Anneal | $\mu_h$ [cm$^2$V$^{-1}$s$^{-1}$] | $I_{ON}/I_{OFF}$ | $|V_{th}|$ [V] | $I_{ON}$ [A] |
|---|---|---|---|---|
| 150° C. | 0.503 | ~10$^1$ | 15 | 4.9 × 10$^{-4}$ |
| 200° C. | 0.736 | ~10$^5$ | 4 | 3.1 × 10$^{-4}$ |

TABLE 3

| Anneal | $\mu_h$ [cm$^2$V$^{-1}$s$^{-1}$] | $I_{ON}/I_{OFF}$ | $|V_{th}|$ [V] | $I_{ON}$ [A] |
|---|---|---|---|---|
| 150° C. | 0.445 | ~10$^5$ | 7 | 2.3 × 10$^{-4}$ |
| 200° C. | 0.489 | ~10$^6$ | 8 | 2.8 × 10$^{-4}$ |

As stated above, performances of devices comprising organic semiconductor materials may be evaluated by charge carrier mobility ($\mu_h$), current on/off ratio ($I_{ON}/I_{OFF}$), threshold voltage ($V_{th}$), and magnitude of the on/off current ($I_{ON}$). The data in Tables 2 and 3 indicate that devices may be fabricated from the novel AMDHP fused-thiophene organic semiconductor polymer disclose herein and that these devices may be operated with predetermined charge mobilities, on/off ratios, threshold voltages, and on/off currents.

In some examples, the AMDHP fused-thiophene organic semiconductor polymers disclosed herein have hole mobilities ($\mu_h$) of 0.1 $cm^2V^{-1}s^{-1}$, 0.5 $cm^2V^{-1}s^{-1}$, 1 $cm^2V^{-1}s^{-1}$, 2 $cm^2V^{-1}s^{-1}$, 3 $cm^2V^{-1}s^{-1}$, 4 $cm^2V^{-1}s^{-1}$, 5 $cm^2V^{-1}s^{-1}$, 10 $cm^2V^{-1}s^{-1}$, or any range defined by any two of those endpoints. The hole mobilities may be equal to or greater than any of these values. In some examples, the AMDHP fused-thiophene organic semiconductor polymers have hole mobilities of 0.1 $cm^2V^{-1}s^{-1}$ to 4 $cm^2V^{-1}s^{-1}$. In some examples, the AMDHP fused-thiophene organic semiconductor polymers have hole mobilities of at least 0.4 $cm^2V^{-1}s^{-1}$, or at least 0.5 $cm^2V^{-1}s^{-1}$, or at least 0.7 $cm^2V^{-1}s^{-1}$.

In some examples, the AMDHP fused-thiophene organic semiconductor polymers disclosed herein have on/off ratios ($I_{ON}/I_{OFF}$) of greater than $10^1$, or greater than $10^2$, or greater than $10^3$, or greater than $10^4$, or greater than $10^5$, or greater than $10^6$.

In some examples, the AMDHP fused-thiophene organic semiconductor polymers disclosed herein have threshold voltages ($V_{th}$) in thin film transistor devices of 1V, 2V, 3V, 4V, 5V, 10V, 15V, 20V or any range defined by any two of those endpoints. In some examples, the AMDHP fused-thiophene organic semiconductor polymers have a threshold voltage of between 1V and 4V, or between 4V and 8V, or between 8V and 12V, or between 12V and 16V in thin film transistor devices. In some examples, the AMDHP fused-thiophene organic semiconductor polymers have a threshold voltage of less than 5V or less than 1V.

Molecular modeling confirms that repeat units of copolymers of fused thiophene with AMDHP have lower reorganization energies than repeat units of copolymers of fused thiophene with other acceptors (e.g., diketopyrrolopyrrole, DPP). This indicates that for similar structures and molecular weights (Mw), copolymers of fused thiophene with AMDHP may have higher mobilities than copolymers of fused thiophene with DPP.

FIGURE illustrates a plot of drain current as a function of gate voltage from an OTFT device prepared with dialkoxydimethylenedihydropyrazine (AMDHP) fused-thiophene (FT) organic semiconductor polymers presented herein. The arrows in the FIGURE indicate on which axes the curves are plotted. In other words, the line only curves are plotted on the left axis (drain current, (A)), while the dot-and-line curves are plotted on the right axis (drain current$^{0.5}$ ($A^{0.5}$)). The line only curves illustrate directly-measured data. The dot-and-line curves illustrate the square root of the directly-measured data. The square root plot is needed to obtain derived parameters, such as device charge mobility (i.e., slope of the square root curve). The similarities between the two line only curves and the two dot-and-line curves indicate replicabilities of different devices.

Thus, as presented herein, a new combination of fused thiophenes with dialkoxydimethylenedihydropyrazine (AMDHP) is disclosed having desired electrical properties and solubility in common organic solvents (e.g., toluene).

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

As utilized herein, "optional," "optionally," or the like are intended to mean that the subsequently described event or circumstance can or cannot occur, and that the description includes instances where the event or circumstance occurs and instances where it does not occur. The indefinite article "a" or "an" and its corresponding definite article "the" as used herein means at least one, or one or more, unless specified otherwise.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

It will be apparent to those skilled in the art that various modifications and variations can be made without departing from the spirit or scope of the claimed subject matter. Accordingly, the claimed subject matter is not to be restricted except in light of the attached claims and their equivalents.

What is claimed is:

1. A composition, comprising a dialkoxydimethylenedihydropyrazine (AMDHP) fused-thiophene (FT) organic semiconductor polymer having a repeat unit of Formula 2 or Formula 3, or a salt or isomer thereof:

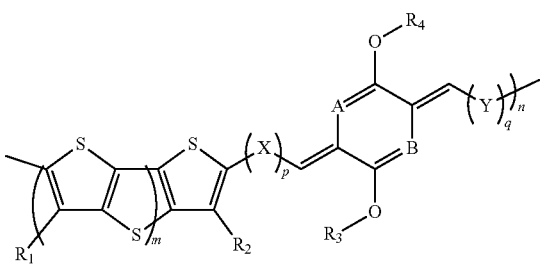

Formula 2

-continued

Formula 3

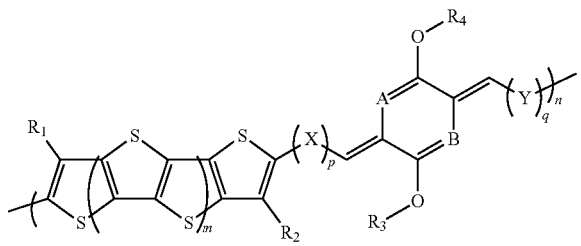

wherein m is an integer greater than or equal to zero;
wherein n is an integer greater than or equal to one;
X and Y are, independently, a covalent bond or aryl;
A and B are, independently, a nitrogen group or a C—H group;
$R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or combinations thereof, with each of the preceding being substituted or unsubstituted;
$R_3$ and $R_4$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or combinations thereof, with each of the preceding being substituted or unsubstituted; and
p and q are, independently, integers greater than or equal to zero.

2. The composition of claim 1, wherein A and B are nitrogen.

3. The composition of claim 1, wherein at least one of $R_1$ and $R_2$ comprises a substituted or unsubstituted alkyl.

4. The composition of claim 3, wherein at least one of $R_1$ and $R_2$ comprises an unsubstituted alkyl.

5. The composition of claim 1, wherein at least one of $R_3$ and $R_4$ comprises a substituted or unsubstituted alkyl.

6. The composition of claim 5, wherein at least one of $R_3$ and $R_4$ comprises a substituted or unsubstituted alkyl group comprising at least six carbon atoms.

7. The composition of claim 1, wherein X and Y are, independently, at least one unfused thiophene groups.

8. The composition of claim 1, wherein p and q are different values.

9. A polymer comprising the composition of claim 1, wherein the polymer has a molecular weight in a range of 4000 Da to 180,000 Da.

10. An organic thin film transistor (OTFT) comprising:
a substrate;
a gate electrode;
a gate dielectric layer;
a patterned source and drain layer; and
an organic semiconductor layer, wherein the organic semiconductor layer comprises a polymer having the composition of claim 1.

11. A device comprising the composition of claim 1 configured in an electronic, optoelectronic, or nonlinear optical device.

12. The device of claim 11, wherein the device comprises a transistor (FET), a thin-film transistor (TFT), an organic light-emitting diode (OLED), an electro-optic (EO) device, a conductive material, a two photon mixing material, an organic semiconductor, a RFID tag, an electroluminescent device, or a photovoltaic and sensor device.

13. A composition having a repeat unit of Formula 4, or a salt or isomer thereof:

Formula 4

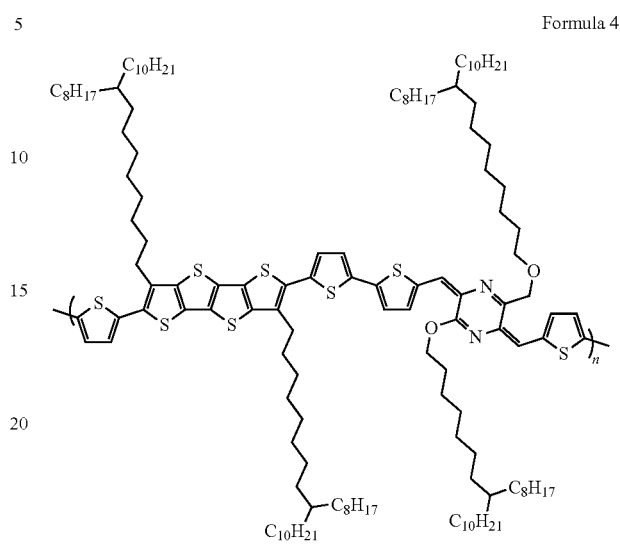

wherein n is an integer greater than one.

14. A method of fabricating a dialkoxydimethylenedihydropyrazine (AMDHP) fused-thiophene (FT) organic semiconductor polymer, comprising:
reacting tin-substituted dialkylated tetrathienoacene or thienyl-dialkylated tetrathienoacene with halogen-substituted thienyl-AMDHP; or
reacting halogen-substituted dialkylated tetrathienoacene or thienyl-dialkylated tetrathienoacene with tin-substituted thienyl-AMDHP.

15. The method of claim 14, wherein the halogen-substituted dialkylated tetrathienoacene comprises:

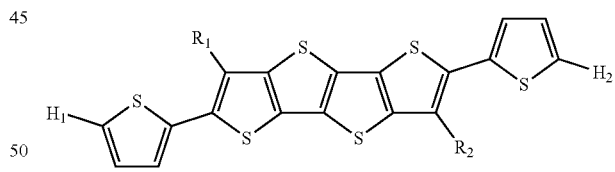

or a salt or isomer thereof,
wherein $H_1$ and $H_2$ are, independently, chlorine (Cl), bromine (Br), and iodine (I), and
wherein $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or combinations thereof, with each of the preceding being substituted or unsubstituted.

16. The method of claim 15, wherein at least one of $H_1$ and $H_2$ are Br.

17. The method of claim 14, wherein the tin-substituted dialkylated tetrathienoacene comprises:

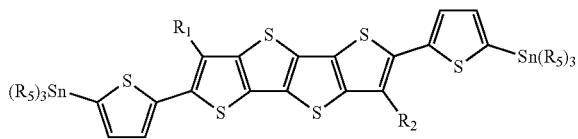

or a salt or isomer thereof, wherein $R_1$, $R_2$, $R_5$, and $R_6$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or combinations thereof, with each of the preceding being substituted or unsubstituted.

18. The method of claim 17, wherein at least one of $R_5$ and $R_6$ are substituted or unsubstituted alkyl groups.

19. The method of claim 14, wherein the thienyl-dialkylated tetrathienoacene comprises:

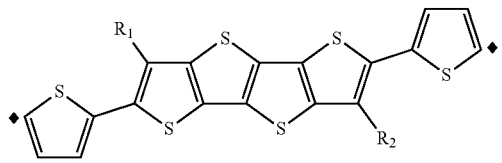

or a salt or isomer thereof, wherein $R_1$ and $R_2$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or combinations thereof, with each of the preceding being substituted or unsubstituted.

20. The method of claim 14, wherein the halogen-substituted thienyl-AMDHP comprises:

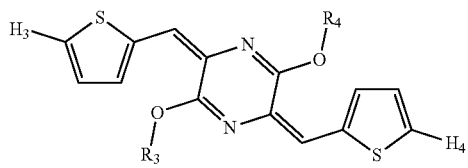

or a salt or isomer thereof, wherein $H_3$ and $H_4$ are, independently, chlorine (Cl), bromine (Br), and iodine (I), and wherein $R_3$ and $R_4$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or combinations thereof, with each of the preceding being substituted or unsubstituted.

21. The method of claim 20, wherein at least one of $H_3$ and $H_4$ are Br.

22. The method of claim 14, wherein the tin-substituted thienyl-AMDHP comprises:

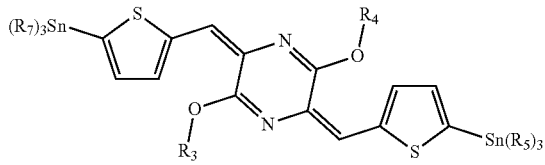

or a salt or isomer thereof, wherein $R_3$, $R_4$, $R_7$, and $R_8$ are, independently, alkyl, alkenyl, alkynyl, aryl, cycloalkyl, aralkyl, amino, ester, aldehyde, hydroxyl, alkoxy, thiol, thioalkyl, halide, acyl halide, acrylate, vinyl ether, or combinations thereof, with each of the preceding being substituted or unsubstituted.

23. The method of claim 22, wherein at least one of $R_7$ and $R_8$ are substituted or unsubstituted alkyl groups.

\* \* \* \* \*

UNITED STATES PATENT AND TRADEMARK OFFICE
CERTIFICATE OF CORRECTION

PATENT NO.         : 10,985,321 B2
APPLICATION NO.    : 16/555548
DATED              : April 20, 2021
INVENTOR(S)        : Mingqian He et al.

It is certified that error appears in the above-identified patent and that said Letters Patent is hereby corrected as shown below:

On the Title Page

In Column 2, item (56), Other Publications, Line 8, delete "Orgainc" and insert -- Organic --, therefor.

In Column 2, item (56), Other Publications, Line 11, delete "Orgainc" and insert -- Organic --, therefor.

In Column 2, item (56), Other Publications, Lines 19-20, delete "Materials:;" and insert -- Materials"; --, therefor.

In Column 2, item (56), Other Publications, Line 22, delete "Mobilites" and insert -- Mobilities --, therefor.

On page 2, in Column 1, item (56), Other Publications, Line 4, delete ""Diketopyrrolophrrole" and insert -- "Diketopyrrolopyrrole --, therefor.

In the Claims

In Column 32, Lines 5-25 (approx.), Claim 13, delete " 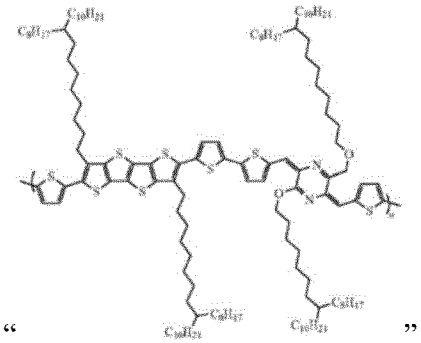 "

Signed and Sealed this
Twentieth Day of September, 2022

Katherine Kelly Vidal
*Director of the United States Patent and Trademark Office*

CERTIFICATE OF CORRECTION (continued)
U.S. Pat. No. 10,985,321 B2 and insert -- 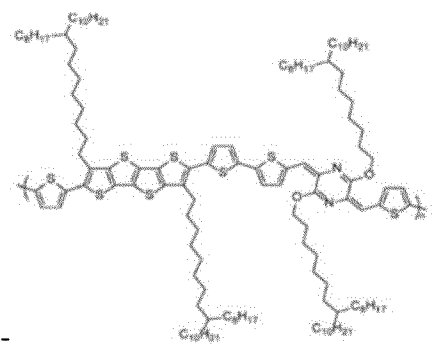 --, therefor.